United States Patent [19]

Oki et al.

[11] 4,267,312

[45] May 12, 1981

[54] ANTHRACYCLINE DERIVATIVES AND PROCESS FOR PREPARING THE SAME

[75] Inventors: Toshikazu Oki, Yokohama; Akihiro Yoshimoto, Fujisawa; Taiji Inui, Chigasaki; Tomio Takeuchi; Hamao Umezawa, both of Tokyo, all of Japan

[73] Assignee: Sanraku-Ocean Co., Ltd., Tokyo, Japan

[21] Appl. No.: 75,302

[22] Filed: Sep. 12, 1979

[30] Foreign Application Priority Data

Sep. 20, 1978 [JP] Japan .................................. 53-115507

[51] Int. Cl.$^3$ ....................... A61K 31/71; C07H 15/24
[52] U.S. Cl. .................................. 536/17 A; 424/181; 435/78
[58] Field of Search ....................................... 536/17 A

[56] References Cited

U.S. PATENT DOCUMENTS

| | | | |
|---|---|---|---|
| 4,039,736 | 8/1977 | Nettleton, Jr. et al. | 536/17 A |
| 4,146,616 | 3/1979 | Penco et al. | 536/17 A |

*Primary Examiner*—Johnnie R. Brown
*Attorney, Agent, or Firm*—Jordan and Hamburg

[57] ABSTRACT

New anthracycline derivatives, 1-hydroxy-13-dihydrodaunomycin and N-formyl-1-hydroxy-13-dihydrodaunomycin are produced by microbial transformation of ε-pyrromycinone and ε-isorhodomycinone with daunomycin-producing streptomyces and their mutants. The derivatives herein are useful as cancer chemotherapeutic agents.

3 Claims, 4 Drawing Figures

FIG. I

ANTHRACYCLINE DERIVATIVES AND PROCESS FOR PREPARING THE SAME

BACKGROUND OF THE INVENTION

This invention relates to new anthracycline derivatives, to their production and recovery, and to their therapeutic use.

A number of anthracycline glycosides have been described in prior literature. Among them, daunomycin and adriamycin are particularly being watched with keen interest by those in the field of cancer chemotherapy and have already been applied clinically for human cancers. Preparation of adriamycin by fermentation of *Streptomyces peuceticus var. caesius* is disclosed in U.S. Pat. No. 3,590,028. Chemical conversion of daunomycin to adriamycin is taught in U.S. Pat. No. 3,803,124. Daunomycin produced by fermentation of *S. peuceticus* in U.K. Pat. No. 1,003,383 is the same as Rhone-Poulenc's 13057RP (see U.K. Pat. Nos. 985,598, 1,188,262 and 1,241,750 and U.S. Pat. No. 3,616,242) and as danubomycin disclosed in U.S. Pat. No. 3,092,550 and U.K. Pat. No. 901,830. Dihydrodaunomycin is disclosed in U.S. Pat. No. 3,686,163. The anthracyclinones, ε-pyrromycinone and ε-isorhodomycinone, were described in U.S. Pat. No. 3,864,480, Keller-Schierlein et al., Antimicrobial Agents and Chemotherapy, page 68 (1970), Chem. Ber. 92:1904(1959), Chem. Ber. 88:1792(1955) and Tetrahedron 19:395(1963). For further illustrative and summary disclosures of anthracycline antibiotics see Index of Antibiotics from Actinomycetes, Volume 2, Hamao Umezawa, Editor-in-Chief, Japan Scientific Societies Press, Tokyo & University Park Press, Baltimore, U.S.A. (1978) as follows:

| ANTIBIOTICS | PAGE NUMBERS |
| --- | --- |
| Aclacinomycin A & B | 101–102 |
| Adriamycin | 122 |
| Carminomycin I | 225 |
| Daunosaminyldaunomycin | 285 |
| Galirubin S-D | 405–408 |
| Rhodomycin X-Y | 879–880 |
| β-Rhodomycins | 881–885 |
| γ-Rhodomycins | 886–892 |
| Steffimycin | 945 |

The textbook, Antibiotics, Vol. 1, Mechanism of Action, edited by D. Gottlieb & P. D. Shaw, Springer-Verlag, New York, Inc., N.Y., N.Y. (1967) on pages 190–210 contains a review of A. DiMarco entitled Daunomycin and Related Antibiotics.

This invention relates to new anthracycline derivatives, to processes for their preparation and to the use of such derivatives in inhibiting the growth and nucleic acid biosynthesis of murine leukemic L1210 cells in culture. More particularly it relates to novel anthracycline glycosides designated herein 1-hydroxy-13-dihydrodaunomycin and N-formyl-1-hydroxy-13-dihydrodaunomycin. The anthracycline derivatives are produced by cultivating a daunomycin-producing strain of streptomyces and blocked mutants therefrom with ε-pyrromycinone and ε-isorhodomycinone in an aqueous nutrient medium containing assimilable sources of carbon, nitrogen, inorganic salts and other nutrients necessary for the growth of the microorganism under submerged aerobic conditions until a substantial amount of new anthracycline derivatives are produced by said microorganism in said culture medium and recovering 1-hydroxy-13-dihydrodaunomycin and N-formyl-1-hydroxy-13-dihydrodaunomycin from the culture broth. ε-Pyrromycinone or ε-isorhodomycinone was added to the growing culture during the logarithmic phase of streptomyces at the concentration of 10–200 μg/ml, and the glycosidation of aglycone is completed by further aerobic cultivation for 18 to 72 hours. 1-Hydroxy-13-dihydrodaunomycin and N-formyl-1-hydroxy-13-dihydrodaunomycin were recovered and separated by extraction of the whole fermentation broth, with or without the separation of mycelium, or by extraction from mycelium followed by separation and isolation of the component glycosides by standard column chromatographic procedures. 1-Hydroxy-13-dihydrodaunomycin and N-formyl-1-hydroxy-13-dihydrodaunomycin showed a marked antitumor activity in leukemic L1210-bearing mice and lower toxicity than daunomycin in mice.

This invention also embraces 1-hydroxy-13-dihydrodaunomycin and N-formyl-1-hydroxy-13-dihydrodaunomycin as crude solid, as purified solids, and as their non-toxic acid addition salts.

DETAILED DESCRIPTION OF THE INVENTION

Figure 1:
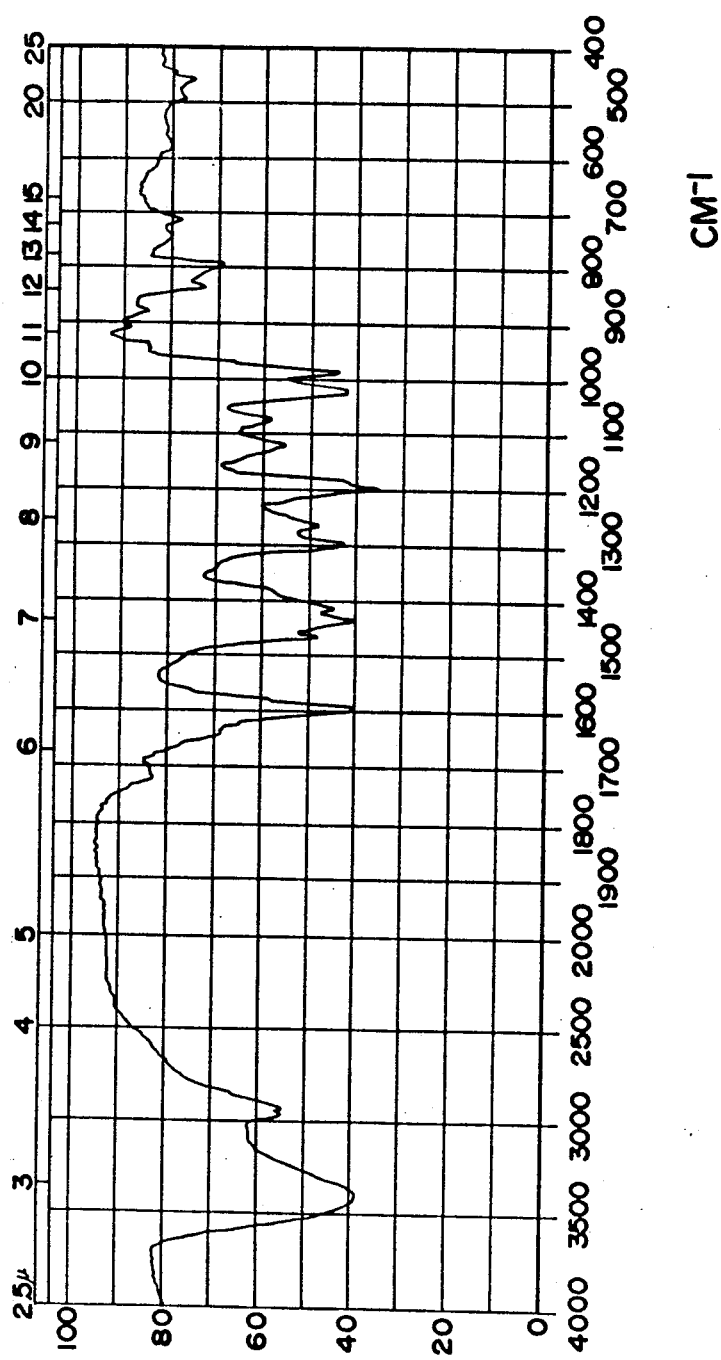
FIG. 1 shows the infrared absorption spectrum of 1-hydroxy-13-dihydrodaunomycin when pelleted in potassium bromide.

The present invention provides the novel anthracycline glycoside derivatives of the general formula

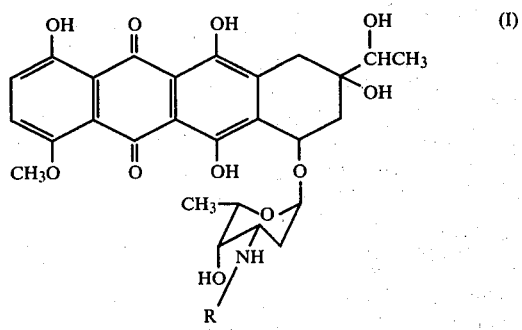

wherein R represents a hydrogen atom or a formyl group (—CHO) and the non-toxic addition salts, and to a process for the preparation thereof.

The present inventors have discovered two new and low toxic anthracycline glycosides which were formed by microbial conversion of ε-pyrromycinone or ε-isorhodomycinone using a daunomycin-producing strain or mutant therefrom after extensive studies on the production of more useful derivatives with low toxicity and more potent antitumor activity than adriamycin and daunomycin which are widely used as cancer chemotherapeutic agents. The inventors first established that a biologically inactive anthracyclinone aglycone is converted to new biologically active anthracycline glycosides by the use of microorganisms.

The process for preparation of the novel anthracycline derivatives in the present invention is as follows.

The starting materials in the present invention are ε-pyrromycinone and ε-isorhodomycinone, as shown in the formula

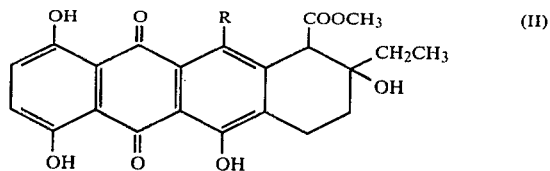

wherein R represents a hydrogen atom in ε-pyrromycinone and a hydroxyl group in ε-isorhodomycinone.

The compounds of the present invention are produced by fermentation of various daunomycin-producing strains of streptomyces including several known daunomycin, carminomycin and adriamycin-producing strains such as *Streptomyces coeruleorubidus* ME130-A4 (FERM P-3450), *S. peuceticus* subsp. *carneus* ATCC 21345, *S. coeruleorubidus* ATCC 13740, *S. peuceticus* subsp. *caestus* NRRL B-5337, *S. peuceticus* NRRL B-3826 and various mutants thereof obtained by the treatment of ultraviolet irradiation or NTG. Mutant strains incapable of producing pigments in the fermentation broths are especially preferred. For instance, non-pigment producing mutants 1U-222, 1N-372 and 1N-479 of *S. coeruleorubidus* are most preferably used for the present invention.

Production of the compounds of the present invention is carried out by cultivating a strain capable of converting ε-pyrromycinone or ε-isorhodomycinone to said compounds in a conventional aqueous nutrient medium containing known nutritional sources for actinomycetes with the addition of ε-pyrromycinone or ε-isorhodomycinone as substrates. Submerged aerobic culture is preferably employed for the production of substantial amounts of the compounds. The general procedures used for the cultivation of other actinomycetes are applicable to the cultivation according to this invention. For example, streptomyces culture grown on an agar slant containing 0.3% yeast extract, 1% soluble starch and 1.5% agar at pH 7.0 and stored at 6° to 7° C. is aerobically cultured for 1 to 2 days at 25° to 32° C. in an aqueous medium containing glucose, starch, organic nitrogen sources and inorganic salts. The above seed culture is then inoculated into an aqueous medium consisting of sucrose, glucose, soybean meal and inorganic salts of 1 to 3% in volume, and aerobically cultured at a conventional temperature ranging from 20° to 37° C., preferably between 25° to 32° C. and at a pH of 6 to 9 for 32 to 100 hours. During the cultivation, ε-pyrromycinone or ε-isorhodomycinone with the concentration of 10 to 200 μg/ml is added to the medium during the logarithmic phase of cell growth after which cultivation is further continued for 18 to 72 hours to complete the biotransformation of anthracyclinone substrate to 1-hydroxy-13-dihydrodaunomycin and N-formyl-1-hydroxy-13-dihydrodaunomycin in either shake flask or submerged aerobic fermentation with aeration and agitation provided as in the examples shown below.

The compounds in the present invention exist intracellularly as well as extracellularly, and thus extracted from mycelium and filtrate after separation of mycelium and filtrate. For extracting the compounds from mycelium, acetone, chloroform, methanol and acidic buffer solution were used. When extracting from the filtrate, chloroform, toluene, ethyl acetate and acidic buffer solution were used. After concentrating in vacuo the extracts were purified by silicic acid and ion-exhange column chromatography and gel filtration using Sephadex LH-20 (cross-linked dextran gels, Pharmacia Fine Chemical AB), carboxy methyl cellulose (Brown Co.,). After concentration of the active eluates, 1-hydroxy-13-dihydrodaunomycin and N-formyl-1-hydroxy-13-dihydrodaunomycin were obtained in purified crystalline powder from a suitable organic solvent.

Elucidation of the structure of the compounds thus obtained in the present invention was carried out by ultraviolet and visible absorption, infrared absorption, 100 MHz proton NMR and mass spectral analyses, which showed that both ε-isorhodomycinone and 1-hydroxy-13-dihydrodaunomycin were the products from mycelium, and both ε-isorhodomycinone and N-formyl-1-hydroxy-13-dihydrodaunomycin were from the filtrate.

It will be readily seen from the structure determination that the compounds in the present invention are novel anthracycline glycosides which contain the same amino sugar i.e. daunosamine and N-formyldaunosamine as known daunomycin and N-formyldaunomycin, but which differ from both the compounds in having novel 1-hydroxy-13-dihydrodaunomycinone aglycone shown above.

The compounds in the present invention form non-toxic acid addition salts with a variety of organic acid and inorganic salt-forming reagents. Thus, acid addition salts formed with such acids as sulfuric, phosphoric, hydrochloric, acetic, propionic, maleic, oleic, citric, succinic, tartaric, glutamic, pantotheic, laurylsulfonic, methanesulfonic, naphtalenesulfonic and related acids can be employed. For the purpose of an anticancer agent, the compounds of free base are equivalent to their non-toxic acid addition salts. Free base of the compounds can be lyophilized with non-toxic acid in the proper solution or acid addition salts can be recovered by precipitation from solvents capable of slightly dissolving their non-toxic acid addition salts. These acid addition salts can be changed in their original free base form by neutralizing with basic compounds.

The following describes the usefulness of 1-hydroxy-13-dihydrodaunomycin and N-formyl-1-hydroxy-13-dihydrodaunomycin in the present invention.

(1) The compounds in the present invention markedly inhibited the growth and nucleic acid biosynthesis of murine leukemic L1210 cells in culture. For example, L1210 cells were inoculated into a RPMI 1640 medium (Nissui, Rosewell Park Memorial Institute 1640) containing 20% calf serum at the cell density of $5 \times 10^4$ cells/ml and the compound in the present invention was simultaneously added to the medium at the concentration of 0.1 and 0.5 μg/ml and cultivated at 37° C. in a $CO_2$ incubator. 1-Hydroxy-13-dihydrodaunomycin inhibited 10.8% and 52.2% of control growth at 0.1 and 0.5 μg/ml, respectively, and N-formyl-1-hydroxy-13-dihydrodaunomycin showed 16% inhibition of control at 0.5 μg/ml.

(2) L1210 cells were inoculated at $5 \times 10^5$ cells/ml into a RPMI 1640 medium containing 10% calf serum and cultivated at 37° C. for 1 to 2 hours in a $CO_2$ incubator. The compound in the present invention at various concentrations and $^{14}C$-thymidine (0.05 μCi/ml) or $^{14}$C-uridine (0.05 μCi/ml) were added and incubated at 37° C. for 60 min. After stopping the pulse-labeling by addition of 10% trichloroacetic acid (TCA) to the reaction mixture, acid-insoluble materials were precipitated, washed 3 times with 5 to 10% TCA, and dissolved in a small amount of formic acid, and then the radioactivity of the solution was determined. Effects on the biosynthesis of DNA and RNA were shown by the 50% inhibition concentration ($IC_{50}$) of the incorporation of radioactivity into acid-insoluble materials. $IC_{50}$ of 1-hydroxy-13-dihydrodaunomycin was 3.8 and 1.8 μg/ml for $^{14}$C-thymidine and $^{14}$C-uridine, respectively, and $IC_{50}$ of N-formyl-1-hydroxy-13-dihydrodaunomycin was over 2.5 μg/ml for the incorporation of both precursors.

(3) It was also demonstrated that the compounds in present invention showed a marked antitumor activity against experimental tumors with lower toxicity in animals than daunomycin. For example, $BDF_1$ mice were inoculated intraperitoneally with $1 \times 10^6$ cells/mouse. 24 hours after inoculation, the compound was intraperitoneally injected once daily for 10 days consecutively. On day 45, the % of prolongation of the survival time to control was 161 to 185% at 2.5 to 5 mg/kg/day of 1-hydroxy-13-dihydrodaunomycin and 135 to 148% at 2.5 to 5 mg/kg/day of N-formyl-1-hydroxy-13-dihydrodaunomycin. At the dose of 10 mg/kg/day weight loss was observed, but general toxicity was less than daunomycin.

Mutagenicity of 1-hydroxy-13-dihydrodaunomycin and N-formyl-1-hydroxy-13-dihydrodaunomycin was examined to decrease about a half of daunomycin by the Ames' test using *Sal. typhimurium*.

The following examples are provided for illustrative purposes only and are not intended to limit the scope of the invention.

EXAMPLE 1

Production of 1-hydroxy-13-dihydrodaunomycin

A nutrient medium having the following composition was prepared:

| | |
|---|---|
| Soluble starch | 1.0% |
| Glucose | 1.0% |
| Meat (Soybean meal, Ajinomoto Co.) | 1.0% |
| $KH_2PO_4$ | 0.1% |
| $MgSO_4 \cdot 7H_2O$ | 0.1% |
| $CuSO_4 \cdot 5H_2O$ | 0.0007% |
| $FeSO_4 \cdot 7H_2O$ | 0.0002% |
| $MnCl_2 \cdot 4H_2O$ | 0.0008% |
| $ZnSO_4 \cdot 7H_2O$ | 0.0002% (pH 7.4) |

100 ml of this medium was sterilized at 120° C. for 15 min. in ten 500 ml-Erlenmyer flasks which were inoculated with a agar slant culture of *Streptomyces coeruleorubidus* ME130-A4 (FERM No. P-3450) by platinum loop, and incubated at 28° C. for 48 hours on a rotary shaker.

15 liters of the previously sterilized medium consisting of 3% glucose, 1% meat, 2% corn steep liquor, 0.1% yeast extract, 0.3% NaCl and 0.2% $CaCO_3$ (pH 7.0) placed into each of three 30 liter stainless steel jar fermentor were aseptically inoculated with 300 ml of the above seed culture. Fermentation was carried out at 28° C. for 48 hours with agitation (257 r.p.m.) and aeration (7.5 l/min.). Then, 200 ml of ε-pyrromycinone solution dissolved in a small amount of methanol (2.0 mg/ml) were added to the above culture broth to bring the final concentration of ε-pyrromycinone in the medium to 27 μg/ml, and the cultivation was further continued for 20 hours. 45 liters of the cultured broth thus obtained was filtered to separate the mycelium and filtrate, and 1-hydroxy-13-dihydrodaunomycin was extracted from mycelium and purified as follows.

About 5 kg of the mycelium was extracted with 30 liters of acetone, concentrated under reduced pressure, and crude material was reextracted with 4 liters and 2 liters of chloroform and concentrated to give 20 g of oily substance. This oily substance was dissolved in 20 ml of a chloroform-methanol mixture (1:2), poured into a column (68 cm high and 5 cm in diameter) filled with Sephadex LH-20, and eluted with a chloroform-methanol mixture (1:2) to remove aglycone-type compounds. Active eluates were again poured onto a Sephadex LH-20 column (26 cm high and 4 cm in diameter), eluting out the oily substances with a toluene-methanol mixture (3:1) and then obtaining a red 1-hydroxy-13-dihydrodaunomycin fraction. After concentrating the resulting red eluates to dryness, the red residue was dissolved in 50 ml of toluene and extracted 4 times with 25 ml of 0.1 M acetate buffer at pH 3.0. 100 ml of the resulting aqueous layer was adjusted to a pH of 7.0 with 4 N NaOH aqueous solution, treated with 50 ml of chloroform to remove a small amount of impurities, reextracted twice with 50 ml of n-butanol, and then concentrated to dryness.

To remove inorganic salts as precipitate, the resulting red residue was dissolved and concentrated to give 158 mg of crude substance. The crude substance was dissolved in 2 ml of M/50 acetate buffer at pH 5.0 and poured onto a CM-cellulose column (5 cm high and 1.5 cm in diameter). After washing the column with 30 ml of 50/M acetate buffer (pH 5.0) the adsorbed active substance was eluted with a small amount of N/50 hydrochloric acid aqueous solution. The active eluate was extracted with n-butanol after adjusting the pH to 7.0 with 1 N NaOH aqueous solution, concentrated to dryness, and dissolved in 1 ml of methanol. Finally, 29.5 mg of red purified powder was obtained by column chromatography of Sephadex LH-20 with methanol and then concentrated to dryness.

The purified compound has the following properties:
m.p. 188°–190° C.

UV $\lambda_{max}^{nm}$ ($E_{1 cm}^{1\%}$ in methanol); 240(720), 285(123), 520(239), 546(216), 600(42).

IR: FIG. 1 (KBr); 3400, 2900–3000, 1590, 1260, 1195, 1020, 980 $cm^{-1}$

Figure 2:
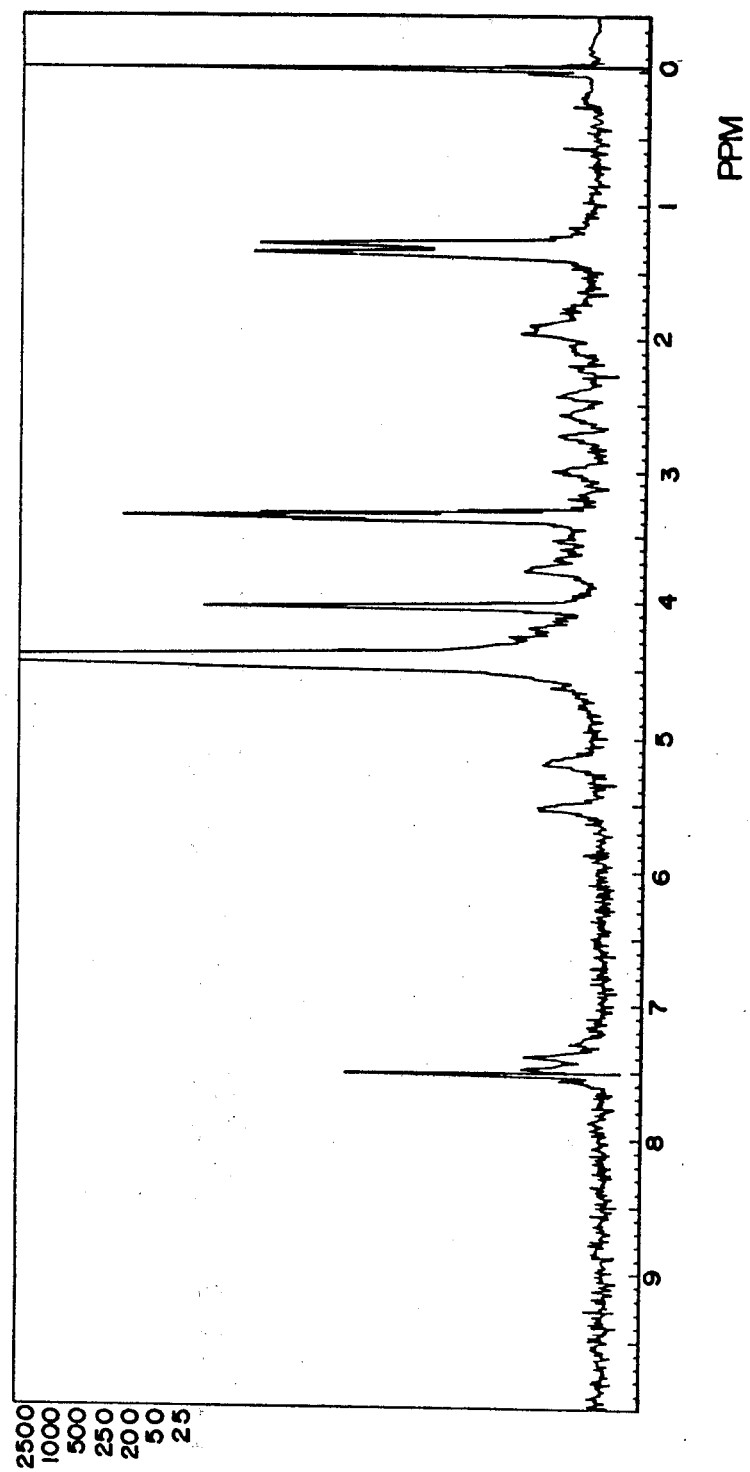
FIG. 2 shows the NMR spectrum of 1-hydroxy-13-dihydrodaunomycin in $CDCl_3:CD_3OD=1:1$ (100 MHz).

NMR: FIG. 2 (100 MHz, $CDCl_3:CD_3OD = 1:1$)

The structure of an aglycone obtained by acid hydrolysis was confirmed to be 1-hydroxy-13-dihydrodaunomycinone by having m/e 416 ($M^+$) on mass spectral analysis. Its configuration was 7S, 9S in the CD spectrum.

EXAMPLE 2

Production of N-formyl-1-hydroxy-13-dihydrodaunomycin

N-formyl-1-hydroxy-13-dihydrodaunomycin was isolated from the filtrate obtained in Example 1.

40 liters of the filtrate was extracted twice with chloroform (20+10 liters), concentrated under reduced pressure, poured onto a Sephadex LH-20 column (68 cm high and 5 cm in diameter), and eluted with a toluene-methanol mixture (3:1) after removing the oily substance and aglycone fractions. The concentrate was extracted three times with 10 ml of 0.1 M acetate buffer (pH 3.1), and the aqueous layer was adjusted to a pH of 6.5 with 4 N-NaOH aqueous solution and then reextracted twice with 30 ml of chloroform. The chloroform layer was concentrated under reduced pressure to give 98 mg of crude powder. The crude powder was further purified by silicic acid thin-layer chromatography. A red band separated on the silica gel thin-layer by developing with chloroform-methanol (10:1) was scratched off, extracted with a chloroform-methanol mixture (5:1), concentrated under reduced pressure, and poured onto a Sephadex LH-20 column (42 cm high and 1.8 cm in diameter). 12 g of red powder was obtained by eluting with methanol and concentrating to dryness.

The purified compound has the following properties: m.p. 179°–180° C.

UV $\lambda_{max}{}^{nm}$ ($E_{1\,cm}{}^{1\%}$ in methanol); 240(760), 285(123), 520(258), 548(241), 600(61).

Figure 3:
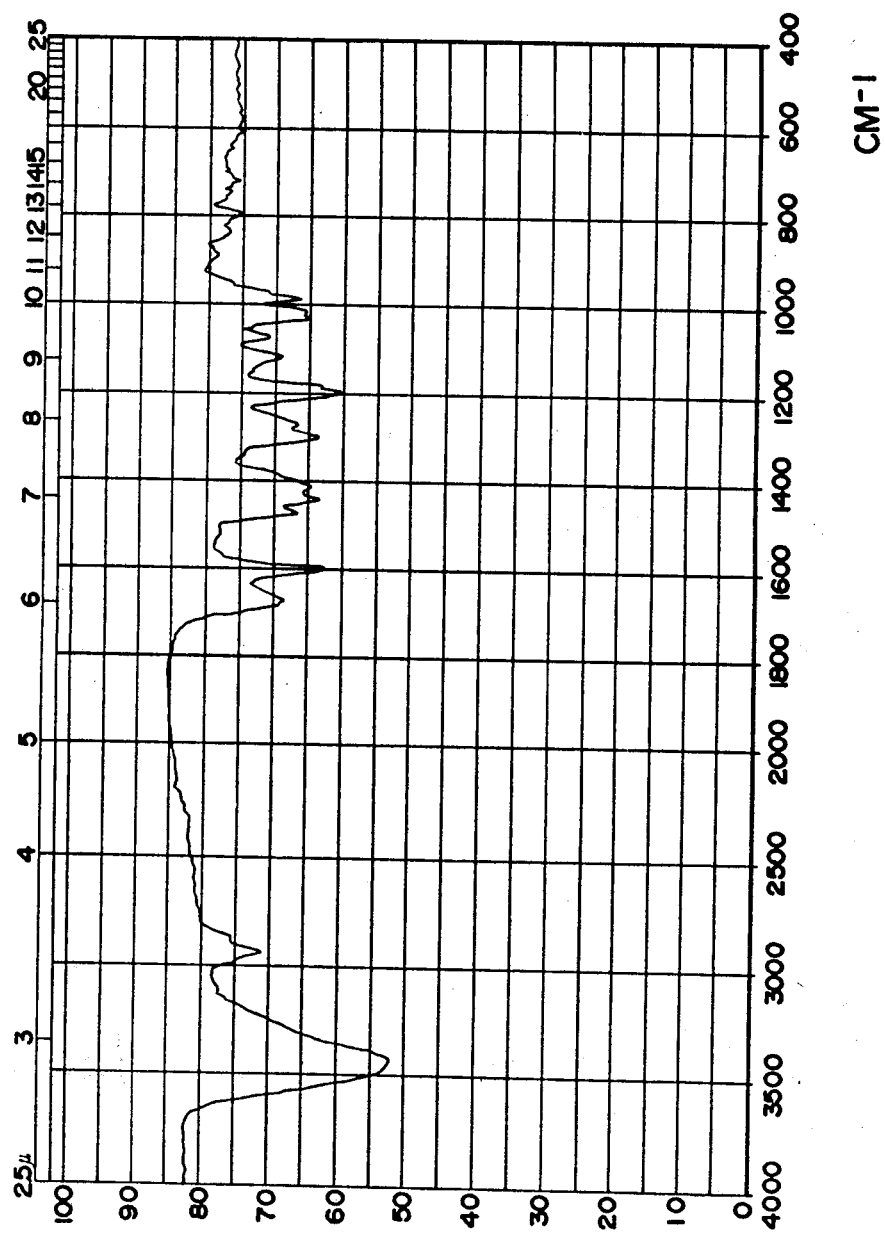
FIG. 3 shows the infrared absorption spectrum of N-formyl-1-hydroxy-13-dihydrodaunomycin when pelleted in potassium bromide.

IR: FIG. 3 (KBr); 3400, 2900–3000, 1680, 1600, 1270, 1200, 1020, 985 cm$^{-1}$.

Figure 4:
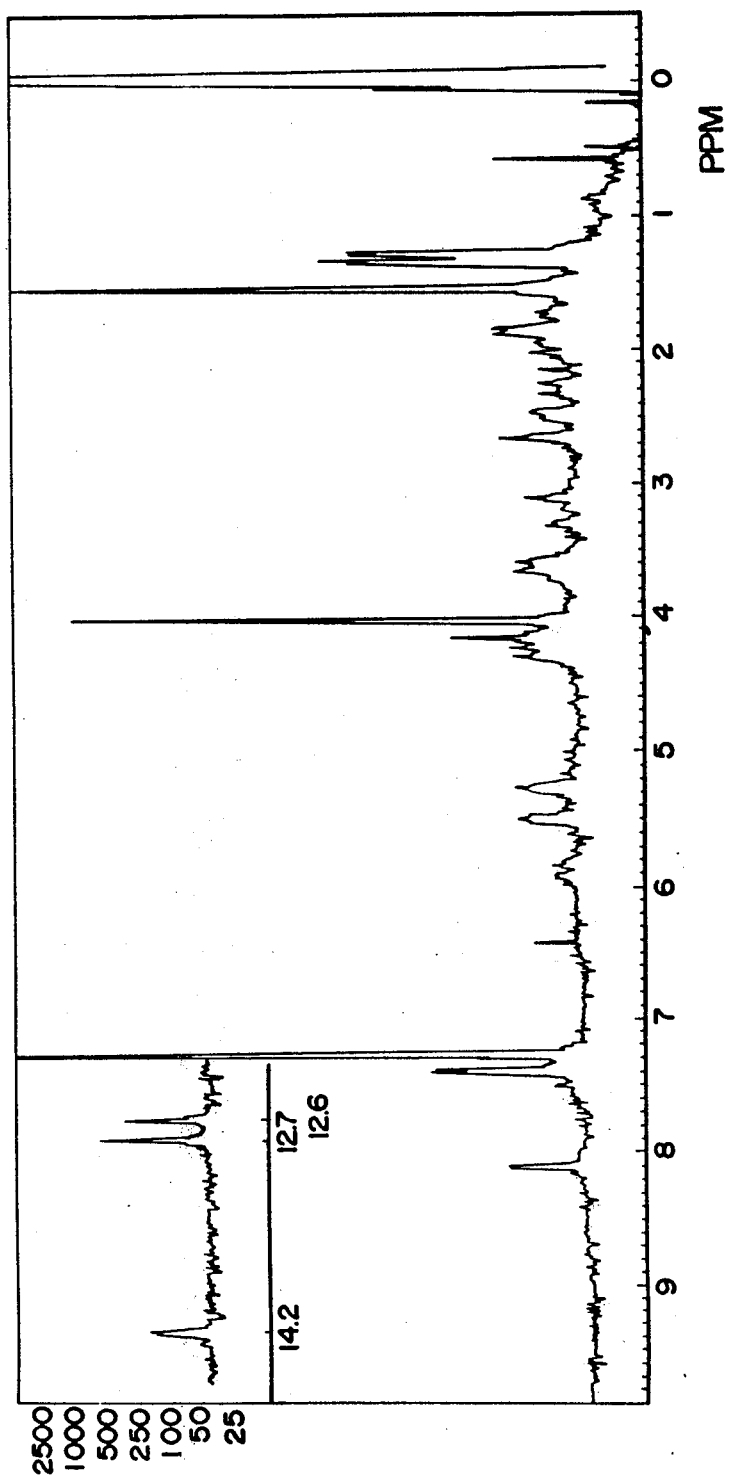
FIG. 4 shows the NMR spectrum of N-formyl-1-hydroxy-13-dihydrodaunomycin in $CDCl_3$ (100 MHz).

NMR: FIG. 4 (100 MHz, CDCl$_3$)

The presence of N-formyl daunosamine was confirmed by the base peak at m/e 158 in CI mass spectrum.

EXAMPLE 3

According to the general method of Examples 1 and 2, 1-hydroxy-13-dihydrodaunomycin and N-formyl-1-hydroxy-13-dihydrodaunomycin were obtained as follows using the indicated streptomyces strains.

A nutrient medium consisting of the following composition was prepared:

| Sucrose | 4% |
|---|---|
| Prorich (Soybean meal, Ajinomoto Co.) | 2.5% |
| NaCl | 0.25% |
| CaCO$_3$ | 0.32% |
| CuSO$_4$ . 5H$_2$O | 0.0005% |
| ZnSO$_4$ . 7H$_2$O | 0.0005% |
| MnCl$_2$ . 4H$_2$O | 0.0005% (pH 7.4) |

After 50 ml of this medium was sterilized at 120° C. for 15 min. in a 500-ml Erlenmyer flask, 1% of the seed culture prepared according to Example 1 was inoculated, and incubated at 28° C. for 90 hours on a rotary shaker. 2 ml of methanol solution of ε-pyrromycinone (2 mg/ml) was then added to the above culture at the concentration of 80 μg/ml, and cultivation further continued for 48 hours to complete the biotransformation.

10 liters of the culture broth was treated and purified according to the method of Example 1, and 1-hydroxy-13-dihydrodaunomycin (1) and N-formyl-1-hydroxy-13-dihydrodaunomycin (2) were obtained as follows:

| Strains | Compound Obtained | |
|---|---|---|
|  | (1) | (2) |
| *Streptomyces coeruleorubidus* ME130-A4 (FERM P-3450) | 15.4 | 4.2 |
| *Streptomyces coeruleorubidus* (ATCC 13740) | 8.1 | 3.2 |
| *Streptomyces peuceticus* subsp. carneus (ATCC 21354) | 6.2 | 2.7 |
| *Streptomyces peuceticus* subsp. caestus (NRRL B5337) | 4.7 | 1.8 |
| *Streptomyces peuceticus* NRRL B3826 | 4.3 | 0.6 |
| *Streptomyces coeruleorubidus* ME130-A4-1U-222 | 18.7 | 2.4 |
| *Streptomyces coeruleorubidus* ME130-A4-1N-372 | 25.3 | 6.3 |
| *Streptomyces coeruleorubidus* ME130-A4-1N-479 | 17.6 | 3.4 |

EXAMPLE 4

According to the same fermentation and purification procedures as described in Examples 1 and 2, 40.5 mg of red powder of 1-hydroxy-13-dihydrodaunomycin and 16.8 mg of red powder of N-formyl-1-hydroxy-13-dihydrodaunomycin were obtained by addition of 200 ml of 2 mg/ml ε-isorhodomycinone substrate (final concentration: 27 μg/ml).

What we claim is:

1. An anthracycline glycoside of the general formula (I)

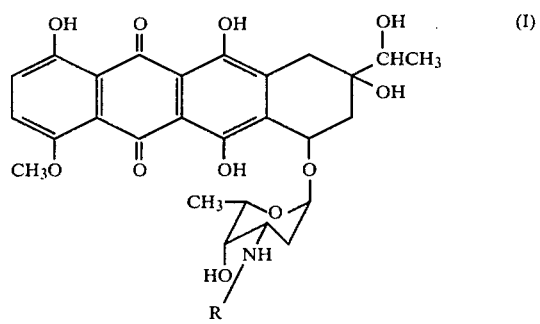

wherein R represents a hydrogen atom or a formyl group (—CHO) or a non-toxic acid addition salt thereof.

2. An anthracycline glycoside 1-hydroxy-13-dihydrodaunomycin of the formula

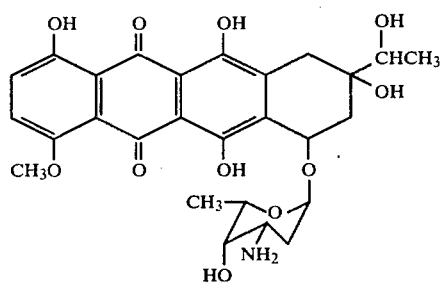

wherein R in the formula I is a hydrogen atom or a non-toxic acid addition salt thereof.

3. An anthracycline glycoside N-formyl-1-hydroxy-13-dihydrodaunomycin of the formula

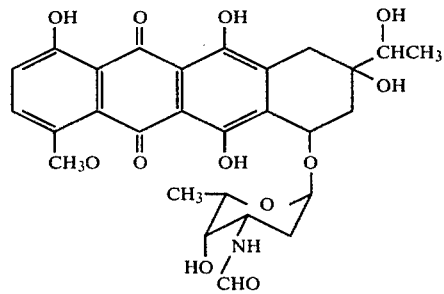

wherein R in the formula I is a formyl group or a non-toxic acid addition salt thereof.

* * * * *